United States Patent [19]
Siele et al.

[11] 3,939,148

[45] Feb. 17, 1976

[54] PROCESS FOR PREPARING 1,3,5,7-TETRANITRO-1,3,5,7-TETRAAZACYCLOOCTANE

[75] Inventors: Victor I. Siele, Succasunna; Everett E. Gilbert, Morristown, both of N.J.

[73] Assignee: The United States of America as represented by the Secretary of the Army, Washington, D.C.

[22] Filed: Feb. 25, 1974

[21] Appl. No.: 445,738

[52] U.S. Cl. .................................... 260/239 HM
[51] Int. Cl.² .................................... C07D 257/02
[58] Field of Search ......................... 260/239 HM

[56] References Cited
FOREIGN PATENTS OR APPLICATIONS
590,851   1/1960   Canada ..................... 260/239 HM

OTHER PUBLICATIONS

Smalin et al. "S-Triazines and Derivatives" Interscience 1969) pp. 566 and 567.

Richmond, J.A.C.S. Vol. 70, pp. 3659–3664 (1948).

*Primary Examiner*—Alton D. Rollins
*Assistant Examiner*—D. B. Springer
*Attorney, Agent, or Firm*—Nathan Edelberg; Robert P. Gibson; A. Victor Erkkila

[57] ABSTRACT

1,3,5,7-tetranitro-1,3,5,7-tetraazacylooctane is prepared by nitrolysis of a 1,3,5,7-tetraacyl-1,3,5,7-tetraazacylooctane or a 1,5-diacyl-3,7-dinitro1 1,3,5,7-tetraazacyloocatne with nitrogen pentoxide.

18 Claims, No Drawings

PROCESS FOR PREPARING 1,3,5,7-TETRANITRO-1,3,5,7-TETRAAZACYCLOOCTANE

BACKGROUND OF THE INVENTION

HMX (1,3,5,7-tetranitro-1,3,5,7-tetraazacyclooctane) is the most powerful non-atomic explosive in military use, but widespread use of this explosive has been limited by its excessive cost. Although HMX was first discovered in 1941, the only known process for its manufacture comprises nitrolysis of hexamethylenetetramine with a mixture of nitric acid and acetic anhydride, essentially as described by Castorina and coworkers (J.A.C.S., 82, 1617 (1960)). This process has deficiencies, notably poor yield of HMX on a methylene basis and high consumption of acetic anhydride.

It has been proposed to produce HMX by nitrolysis of TAT (1,3,5,7-tetraacetyl-1,3,5,7-tetraazacyclooctane). However, such attempts have been unsuccessful (G. C. Bassler, "The Chemistry of Cyclonite," PhD Thesis 1943, Pennsylvania State College, pages 179–180). These attempts have included treatment of TAT with (a) 100% nitric acid at temperature ranging from −30°C. to −50°C., (b) mixtures of ammonium nitrate +acetic anhydride at 70°C., and (c) mixtures of 100% nitric acid and acetic anhydride at temperatures from 0°C. to 25°C. The first two procedures gave no water-insoluble products, while the last produced a water-insoluble compound, which was not HMX.

SUMMARY OF THE INVENTION

An object of the present invention is to provide a process for producing HMX by nitrolysis of TAT. Other objects will become apparent from the following description of the invention.

We have now discovered the HMX can be obtained in good yields by reacting TAT with nitrogen pentoxide. Preferably, an amount of nitrogen pentoxide substantially greater than the stoichiometric amount required for the reaction is employed, particularly to compensate for loss of relatively unstable nitrogen pentoxide due to increased rate of decomposition thereof at the reaction temperature. The nitrogen pentoxide may be introduced as such into the reaction mixture, or it may be generated in situ by employing a mixture of nitric acid with a substance which is capable of reacting with nitric acid under the conditions to produce nitrogen pentoxide.

The process of the present invention is considered to be unobvious in view of the fact that prior art attempts to produce HMX by nitrolysis of TAT have been unsuccessful, even when 100% nitric acid mixed with acetic anhydride was employed, as noted above.

We have also discovered that in place of TAT other 1,3,5,7-tetraacyl-1,3,5,7-tetraazacyclooctanes as well as 1,5-diacyl-3,7-dinitro-1,3,5,7-tetraazacyclooctanes of the general formula shown below can be employed as starting materials in similar manner. The reaction is represented by the following equation wherein R is an alkyl radical containing 1 to 6 carbon atoms, M in both cases is either a nitro group or an acyl radical of the formula RCO— wherein R has the aforesaid definition, and X is 2 when M is a nitrogroup and 4 when M is an acyl radical RCO.

DESCRIPTION OF THE PREFERRED EMBODIMENTS

The following examples illustrate specific embodiments of the method of carrying out the process of the present invention. It is to be understood that they are illustrative only and do not in any way limit the invention.

EXAMPLE 1

Nitration of TAT with a mixture of nitric acid and phosphorus pentoxide 30 grams of 98% nitric acid were introduced into a 100 ml. round bottom, three-neck glass flask provided with a thermometer, magnetic stirring bar, and condenser to which a drying tube filled with calcium sulfate was attached. By means of an external ice-salt bath the flask contents were cooled to 5°C., after which 12 grams of phosphorus pentoxide were added during 15 minutes while vigorously agitating and maintaining the contents at about 5°C. The resulting mixture was allowed to warm to room temperature and 1 gram of TAT was introduced in one portion. The reaction mixture was heated to 50°C. in about 3 minutes with a preheated water bath and agitated at that temperature for one hour. The resulting orange-red solution was then cooled to 20°C. and poured onto 125 grams of ice. After storage of the mixture in the refrigerator for 2 hours, the solid which had separated on quenching was removed by filtration through a sintered glass funnel, washed with cold water until the wash waters were of neutral pH and dried. The crude HMX thus obtained weighed 0.9 gram, possessed a melting point of 273°C. and a purity of 91% as determined by nuclear magnetic resonance (NMR) which corresponds to 79% of the theoretical yield of HMX. The impurities present in the crude product, essentially 1,3,5-trinitro-7-acetyl-1,3,5,7-tetraazacycloctane (SEX), and 1,7-dinitroxy-2,4,6-trinitro-2,4,6-triazaheptane (ATX), can be removed by extraction with boiling acetone.

Table 1 sets forth the results of the above example as well as the results obtained when the reaction was carried out in the foregoing manner but wherein other ratios of phosphorus pentoxide to nitric acid and time and temperature of the reaction were employed.

EXAMPLE 15

Nitration of DADN with $HNO_3$—$P_2O_5$ system 10 grams of phosphorus pentoxide were charged to a 100 ml. round bottom, three-neck glass flask fitted with a condenser, thermometer and a magnetic stirring bar.

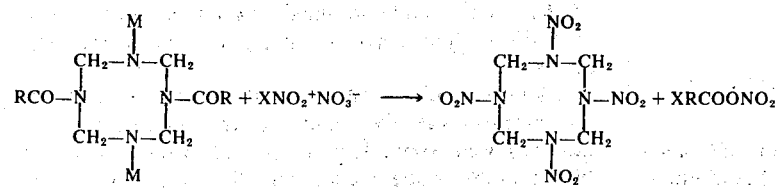

30 grams of 100% nitric acid (freshly distilled from a mixture of 97% nitric acid containing 15% by weight of 30% oleum) were quickly introduced, resulting in a temperature exotherm of about 40°C. The temperature was allowed to cool to 30°–35°C., and 0.89 gram of 1,5-diacetyl-3,7-dinitro-1,3,5,7-tetraazacyclooctane (DADN), prepared by the method described in the Journal of Heterocyclic Chemistry, 10, 725 (1973), was introduced rapidly. The resulting reaction mixture was quickly heated to 65°C. and maintained at that temperature for 15 minutes. The hot reaction mixture was then quenched by pouring it onto a large volume of ice. The resulting precipitate was separated as a cake by filtration, washed acid-free with cold water and air dried. The product thus obtained weighed 0.87 gram and analyzed 100% pure HMX, which corresponds to 98% of theory yield of HMX.

EXAMPLE 16

Nitration of TPT with $HNO_3$—$P_2O_5$ system

The procedure of example 15 was followed but using 1 gram of 1,3,5,7-tetrapropionyl-1,3,5,7-tetraazacyclooctane (TPT), 38 grams of 100% nitric acid and 10 grams of $P_2O_5$. The reaction mixture was heated at 50°C. for 50 minutes, and then drowned and worked up in the aforesaid manner. The product analyzed 100% HMX. The yield of HMX was 94% of theory.

EXAMPLE 17

Nitration of DADN with $HNO_3$-polyphosphoric acid system

The procedure of example 15 was followed using 50 grams of 85% polyphosphoric acid in place of $P_2O_5$, 22.5 grams of 100% $HNO_3$ and 6.1 grams of DADN. The reaction mixture was heated at 60°–70°C. for 60 minutes and then drowned and worked up as above. The product analyzed 100% pure HMX. The HMX was obtained in 88% of theory yield.

Table II shows the results of the foregoing example as well as the results obtained when the reaction was carried out in the foregoing manner but wherein other ratios of polyphosphoric acid, time and temperature of the reaction, etc. were employed.

EXAMPLE 32

Nitration of DADN with $HNO_3$-trifluoroacetic anhydride system 45 grams of 100% nitric acid were charged to a 100 ml. round bottom, three-neck glass flask fitted with a condenser, thermometer and a magnetic stirring bar. The flask contents were cooled to 10°C. and 27.4 grams of trifluoroacetic anhydride followed by 3 grams of DADN were introduced while maintaining the contents at 10°C. The resulting solution was heated rapidly to 50°C. and maintained at that temperature for 1 hour. The reaction mixture was drowned on ice and worked up in the usual manner. 2.5 grams of crude HMX containing 93% HMX and 7% SEX by NMR analysis were thus obtained, corresponding to 76% of theory yield of HMX.

EXAMPLE 33

Nitration of DADN with $HNO_3$-trifluoroacetic anhydride system 27 grams of 100% nitric acid and 35 grams of trifluoroacetic anhydride were added to 25 ml. of cold nitromethane while maintaining the temperature at 10°C. 3 grams of DADN were then added and the resulting solution was heated rapidly to 40°C. and maintained at that temperature for 90 minutes. The reaction mixture was cooled and drowned on ice, and the resulting precipitate was separated by filtration, washed acid-free with water and air dried. 2.86 grams of product analyzing 97% HMX and 3% SEX were obtained, corresponding to 91% of theory yield of HMX.

EXAMPLE 34

Nitration of DADN with $HNO_3$—$SO_3$ system 9 grams of stabilized sulfur trioxide (marketed under the trademark "Sulfan" by Allied Chemical Corp.) were added to 30 grams of 98% nitric acid at 0°C. 3 grams of DADN were added to the mixture, while maintaining the temperature at 5°C. The resulting mixture was heated rapidly to 45°C. and agitated at 45°–50°C. for 70 minutes. The reaction mixture was then quenched on ice and the solid which separated was isolated by filtration, washed acid-free with cold water and dried. 2.1 grams of product, having a melting point of 256°–258°C. and analyzing 89% HMX and 11% SEX by NMR analysis, were thus obtained, corresponding to 60% of the theoretical yield of HMX.

EXAMPLE 35

Nitration of DADN with $N_2O_5$—$HNO_3$ system 20 grams of $N_2O_5$, prepared by reacting phosphorus pentoxide with 98–99% nitric acid according to the procedure of Frankel et al. described in the Journal of Organic Chemistry 25, 747 (1960), were mixed with 30 grams of 100% nitric acid at 0°C. 3 grams of DADN were added to 20 ml. of the resulting solution at 0°C. The solution thus obtained was heated rapidly to 50°C. and agitated at that temperature for 50 minutes. The reaction mixture was drowned on ice and the solid precipitate formed was separated by filtration, washed acid-free and air dried. 1.79 grams of product, which melted at 225°–235°C. and contained 70% HMX and 30% SEX by NMR analysis, were thus obtained, corresponding to 41% of the theoretical yield of HMX.

EXAMPLE 36

Nitration of DADN with $N_2O_5$—$HNO_3$ system 3 grams of DADN were added to 24 grams (15 ml.) of a cold (10°C.) solution of nitrogen pentoxide in nitric acid containing 18% $N_2O_5$ by analysis according to the method of E. Berl, Chem. Ztg. 34, 428 (1910). (The $N_2O_5$—$HNO_3$ solution was prepared by a modification of the Frankel et al. method noted above, wherein an excess of nitric acid was added to $P_2O_5$ and the resulting reaction mixture was distilled in vacuo.) The resulting solution was rapidly heated to 50°C. and agitated at that temperature for 60 minutes. The reaction mixture was then drowned in ice-water mixture, and the solid which precipitated was separated by filtration, washed acid-free with cold water and dried. The product thus obtained weighed 2.66 grams, melted at 264°–266°C. and contained 94% HMX and 6% SEX by NMR analysis, corresponding to 82% of theory yield of HMX.

A kinetic study of nitration rates with various $N_2O_5$ concentrations in $HNO_3$ indicated that the rate of nitration was approximately proportional to the product of the reactant concentration and the $N_2O_5$ concentration. This result indicates that the $N_2O_5$ species, or an ionized form thereof, is the active agent in the nitration of DADN to HMX.

EXAMPLE 37

Nitration of DADN with $N_2O_5$-nitromethane system 12 grams of $N_2O_5$, prepared by reacting phosphorus pentoxide with 98–99% nitric acid according to the procedure of Frankel et al. described in the Journal of Organic Chemistry 25, 747 (1960), were added to 28 grams of nitromethane at 0°C. 3 grams of DADN were added to the resulting solution at 0°C. and the mixture thus obtained was heated to 50°C. and maintained at that temperature for 60 minutes. The reaction mass was drowned in ice-water mixture and the solid precipitate formed was separated by filtration, washed acid-free and dried. The product thus obtained weighed 2.48 grams, melted at 245°–246°C. and contained 80% HMX and 20% SEX based on NMR analysis, which corresponds to 65% of the theoretical yield of HMX.

EXAMPLE 38

Nitration of DPDN with $HNO_3$—$P_2O_5$ system 10 grams of $P_2O_5$ were stirred into 30 grams of 99% nitric acid at room temperature, whereby the mixture heated spontaneously to about 70°C. The mixture was allowed to cool to 30°C. and 1.08 grams of 1,5-dipropionyl-3,7-dinitro-1,3,5,7-tetraazacyclooctane (DPDN) were added quickly and the resulting mixture was heated with agitation to 50°C. for 50 minutes. The reaction mixture was then drowned on ice, and the white solid which precipitated was separated by filtration, washed acid-free with cold water and air dried. The product weighed 0.956 gram, melted at 277°–8°C., and analyzed 100% HMX, corresponding to 89% of the theoretical yield of HMX.

The process of the present invention comprises mixing together the 1,3,5,7-tetraacyl-1,3,5,7-tetraazacyclooctane or the 1,5-diacyl-3,7-dinitro-1,3,5,7-tetraazacyclooctane and nitrogen pentoxide in the presence of an inert liquid diluent, wherein the reactants are at least in part soluble, in sufficient amount to provide a stirrable reaction mixture, usually at a low temperature, e.g. 0°–20°C. to minimize decomposition of the nitrogen pentoxide, which is relatively unstable at higher temperatures, heating the mixture rapidly to reaction temperatures, e.g. about 50°–70°C., and thereafter separating the HMX formed. Suitable diluents, which are inert or practically inert to the reactants, include organic liquids, e.g. nitroparaffins such as nitromethane, chlorinated hydrocarbons, such as methylene chloride and chloroform, as well as inorganic liquids, such as nitric acid. In addition, liquid diluents for the reaction mixture can be provided when a liquid system capable of forming nitrogen pentoxide in situ is employed, e.g. a mixture of nitric acid and polyphosphoric acid, etc., as discussed below.

The amounts of reactants employed in the present process may vary within wide limits. For conversion of 1,5-diacyl-3,7-dinitro-1,3,5,7-tetraazacyclooctane to HMX 2 molecular proportions of $N_2O_5$ are theoretically required in accordance with the equation noted above, while 4 molecular proportions of $N_2O_5$ are required for conversion of 1,3,5,7-tetraacyl-1,3,5,7-tetraazacyclooctane to HMX. Preferably, a substantial excess of $N_2O_5$ over the stoichiometric amount, e.g. about 2 to 50 times the stoichiometric amount, is usually employed, since it appears to ensure a more rapid and efficient conversion to HMX, and also compensates for loss of $N_2O_5$ due to decomposition thereof which is promoted by higher temperatures. The use of still larger proportions of nitrogen pentoxide, although within the scope of the present invention, is relatively uneconomical since it generally provides no additional advantages in yield of HMX, shorter reaction time, etc.

It is not necessary to introduce the nitrogen pentoxide as such to the reaction mixture, but it may be formed in situ from a mixture of nitric acid and a substance capable of reacting with nitric acid to produce nitrogen pentoxide. Thus, for example, $N_2O_5$ can be formed from a mixture of nitric acid and phosphorus pentoxide (Frankel et al. J. Org. Chem 25, 744 (1960), viz.

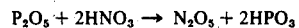

$$P_2O_5 + 2HNO_3 \rightarrow N_2O_5 + 2HPO_3$$

from a mixture of nitric acid and trifluoroacetic anhydride (J. Robson, J.A.C.S. 77, 107 (1955); R. Boschan J. Org. Chem 25, 1450 (1960), viz.

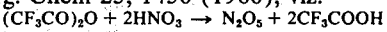

$$(CF_3CO)_2O + 2HNO_3 \rightarrow N_2O_5 + 2CF_3COOH$$

and from a mixture of nitric acid and sulfur trioxide (Farbwerke Hoechst Germ. Pat. 871,744 (1938)), viz.

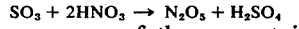

$$SO_3 + 2HNO_3 \rightarrow N_2O_5 + H_2SO_4$$

The process of the present invention is generally carried out at temperatures within the range of 40°C. to 90°C. When substantially lower temperatures are employed, the HMX forming reaction is usually undesirably slow. The use of temperatures substantially above 90°C., although operative to form various amounts of HMX, generally accelerates undesirable side reactions. The particular temperature employed depends on the particular starting material employed, the system used for generating $N_2O_5$, the reaction time desired, the diluent or solvent employed, etc.

Although the order of mixing the reactants is not critical, it is preferred to add the cyclooctane compound to the solution of nitrogen pentoxide in the liquid diluent, or the liquid system for generating nitrogen pentoxide, at a low temperature, e.g. 0°–10°C., and then heat the resulting mixture to the desired reaction temperature. The HMX formed can be recovered by pouring the reaction mixture on ice or ice-water mixture, separating the solid precipitate of HMX by filtration and washing the filter cake acid-free with cold water. The dried HMX can be purified, if necessary, by crystallization from a suitable solvent, such as acetone.

A preferred embodiment of the present process comprises forming the nitrogen pentoxide in situ from a mixture of nitric acid and phosphorus pentoxide, and particularly from a mixture of nitric acid and a polyphosphoric acid containing more than 75% by weight of $P_2O_5$, and especially a polyphosphoric acid containing about 85% by weight of $P_2O_5$. The latter mixture of nitric acid and 85% polyphosphoric acid is especially desirable, since its use in the present process provides a rapid reaction rate and produces HMX in high yield and purity. Also, polyphosphoric acid of approximately 85% content $P_2O_5$ is readily available commercially at relatively low cost and serves as a most desirable liquid diluent in the present process.

When a mixture of nitric acid and 85% commercial polyphosphoric acid is employed to generate $N_2O_5$ in situ, it is advantageous that the polyphosphoric acid constitute the major portion of said mixture. Thus, as shown in examples 17–31, when the polyphosphoric acid constitutes up to about 50% by weight of said mixture, the HMX is obtained in relatively impure form and in yields generally not greater than about 60% of theory, whereas when the proportion of polyphosphoric acid in said mixture is substantially greater than 50% by weight, e.g. about 70%, the HMX is obtained in high purity and in yields of the order of 80–99% of theory.

The foregoing disclosure is merely illustrative of the principles of this invention and are not to be interpreted in a limiting sense. We wish it to be understood that we do not desire to be limited to exact details of construction shown and described for obvious modifications will occur to a person skilled in the art.

wherein R is an alkyl radical of 1 to 6 carbon atoms, and M in both cases is the same and is either a nitro group or an acyl radical of the formula RCO—, wherein R has the aforesaid definition, with nitrogen pentoxide in the presence of a liquid diluent from the group consisting of a nitroparaffin, methylene chloride, chloroform, 100% nitric acid, polyphosphoric acid containing more than 75% by weight of phosphorus pentoxide and a liquid system for producing nitrogen pentoxide consisting essentially of a mixture of 100% nitriacid and a material of the group consisting of trifluoroacetic anhydride, sulfur trioxide, phosphorus pen-

TABLE I

| Ex. No. | TAT Grams | HNO$_3$ Conc. HNO$_3$ (%) | HNO$_3$ Grams | P$_2$O$_5$ Grams | Reaction Conditions Temp. °C. | Reaction Conditions Time (Min.) | Grams | Crude HMX Melting Point °C. | Purity | Impurities | Pure HMX Grams | Pure HMX % Theory |
|---|---|---|---|---|---|---|---|---|---|---|---|---|
| 1 | 1 | 98 | 30 | 12 | 50 | 60 | 0.9 | 270–273 | 91.2 | ATX SEX | 0.82 | 79 |
| 2 | 1 | 98 | 30 | 12 | 58 | 30 | 0.9 | 268–272 | 88.4 | ATX SEX | 0.80 | 76.5 |
| 3 | 1 | 98 | 30 | 9 | 60 | 30 | 0.8 | 267–271 | 85.0 | ATX SEX | 0.68 | 65.4 |
| 4 | 1 | 98 | 30 | 6 | 60 | 60 | 0.63 | 267–270 | 76.0 | ATX SEX | 0.48 | 46.1 |
| 5 | 1 | 98 | 30 | 6 | 60 | 30 | 0.39 | 225–260 | 83.0 | SEX | 0.32 | 31.1 |
| 6 | 1 | 98 | 30 | 6 | 60 | 10 | 0.21 | 217–218 | 33.4 | SEX | 0.7 | 6.7 |
| 7 | 1 | 98 | 30 | 6 | 70 | 10 | 0.38 | 252–260 | 70.6 | ATX SEX | 0.27 | 25.8 |
| 8 | 1 | 98 | 30 | 3 | 70 | 10 | none | — | — | — | — | — |
| 9 | 1 | 98 | 30 | 3 | 70 | 15 | none | — | — | — | — | — |
| 10 | 1 | 98 | 30 | 3 | 25 | 150 | none | — | — | — | — | — |
| 11 | 0.7 | 100 | 21 | 2.1 | 45 | 30 | 0.16 | 219–220 | 10 | SEX | 0.015 | 2.2 |
| 12 | 1 | 100 | 30 | 3 | 70 | 10 | 0.55 | 262–267 | 78 | ATX SEX | 0.43 | 41.3 |
| 13 | 1 | 100 | 30 | 3 | 70 | 120 | none | — | — | — | — | — |
| 14 | 1 | 100 | 30 | 3 | 70 | 30 | 0.78 | 140–260 | 50 | ATX | 0.39 | 37.5 |

TABLE II

| Example No. | DADN Grams | HNO$_3$ Grams | Polyphosphoric Acid* Grams | N$_2$O$_5$ Times Theory** | Temp. °C. | Time Min. | Crude HMX M.P. °C. | Crude HMX % Purity | Pure HMX %Theory |
|---|---|---|---|---|---|---|---|---|---|
| 17 | 8.92 | 22.5 | 50 | 2.9 | 60–70 | 60 | — | 100 | 88 |
| 18 | 5 | 37.4 | 20 | 7.2 | 70 | 5 | 223 | 51 | 34 |
| 19 | 5 | 37.4 | 20 | 7.2 | 70 | 15 | 245 | 83 | 57 |
| 20 | 5 | 37.4 | 20 | 7.2 | 70 | 30 | 276 | 100 | 39 |
| 21 | 5 | 37.4 | 40 | 8.6 | 70 | 15 | 228 | 70 | 47 |
| 22 | 5 | 37.4 | 40 | 8.6 | 70 | 30 | 273 | 82 | 56 |
| 23 | 3.1 | 45 | 100 | 17.2 | 60–70 | 60 | — | 100 | 86 |
| 24 | 3.1 | 22.5 | 50 | 8.4 | 60–70 | 60 | — | 100 | 94 |
| 25 | 2.88 | 22.5 | 50 | 8.0 | 60–70 | 30 | — | 100 | 96 |
| 26 | 2.52 | 22.5 | 50 | 10.2 | 60–70 | 60 | — | 100 | 99 |
| 27 | 6.0 | 22.5 | 50 | 4.3 | 60–70 | 60 | — | 100 | 92 |
| 28 | 6.97 | 22.5 | 50 | 3.7 | 60–70 | 60 | — | 96.5 | 96.5 |
| 29 | 7.6 | 22.5 | 50 | 3.4 | 60–70 | 60 | — | 100 | 84 |
| 30 | 7.5 | 22.5 | 50 | 3.4 | 60–70 | 30 | — | 86 | 74 |
| 31 | 9.1 | 22.5 | 50 | 2.84 | 60–70 | 45 | — | 93 | 77 |

*Commercial 85% polyphosphoric acid, i.e. containing 85% by weight P$_2$O$_5$
**2 mols of N$_2$O$_5$ are theoretically required to convert DADN to HMX as noted above. The figure shown corresponds to the amount of N$_2$O$_5$ formed from the amounts of HNO$_3$ and polyphosphoric acid employed calculated on the basis of the following reaction and assuming that the polyphosphoric acid is H$_2$P$_2$O$_6$ or H$_2$O/P$_2$O$_5$ = 1:1 (molar basis), P$_2$O$_5$ + 2HNO$_3$ → N$_2$O$_5$ + 2HPO$_3$

What is claimed is:

1. A process for preparing 1,3,5,7-tetranitro-1,3,5,7-tetraazacyclooctane, which comprises the step of reacting an N-acylated-1,3,5,7-tetraazacyclooctane of the following formula

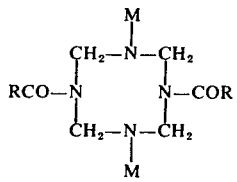

toxide and polyphosphoric acid containing more than 75% by weight of phosphorus pentoxide.

2. The process according to claim 1, wherein the reaction is carried out at a temperature between about 40°C. and about 90°C.

3. The process according to claim 1, wherein at least about 2 times the stoichiometric amount of nitrogen pentoxide required for the reaction is employed.

4. The process according to claim 1, wherein M is nitro.

5. The process according to claim 4, wherein R is methyl.

6. The process according to claim 1, wherein the diluent is nitric acid.

7. The process according to claim 1, wherein the diluent is nitromethane.

8. The process according to claim 1, wherein the nitrogen pentoxide is formed in situ from a mixture of 100% nitric acid and a material selected from the group consisting of trifluoroacetic anhydride, sulfur trioxide, phosphorus pentoxide and polyphosphoric acid containing more than 75% by weight of phosphorus pentoxide.

9. The process according to claim 8, wherein the nitrogen pentoxide is formed in situ from a mixture of nitric acid and trifluoroacetic anhydride.

10. The process according to claim 8, wherein the nitrogen pentoxide is formed in situ from a mixture of nitric acid and sulfur trioxide.

11. The process according to claim 8, wherein the nitrogen pentoxide is formed in situ from a mixture of nitric acid and phosphorus pentoxide.

12. The process according to claim 8, wherein the nitrogen pentoxide is formed in situ from a mixture of 100% nitric acid and polyphosphoric acid containing more than 75% by weight of phosphorus pentoxide.

13. The process according to claim 12, wherein the polyphosphoric acid contains about 85% of phosphorus pentoxide.

14. The process according to claim 13, wherein the mixture of nitric acid and polyphosphoric acid contains more than 50% by weight of polyphosphoric acid.

15. The process according to claim 14, wherein the N-acylated compound is 1,5-diacetyl-3,7-dinitro-1,3,5,7-tetraazacyclooctane.

16. The process according to claim 8, wherein M is nitro.

17. The process according to claim 8, wherein the N-acylated compound is 1,5-diacetyl-3,7-dinitro-1,3,5,7-tetraazacyclooctane.

18. The process according to claim 8, wherein the N-acylated compound is 1,3,5,7-tetraacetyl-1,3,5,7-tetraazacyclooctane.

* * * * *